US008377125B2

(12) United States Patent  (10) Patent No.: US 8,377,125 B2
Kellan  (45) Date of Patent: Feb. 19, 2013

(54) INTRAOCULAR LENS WITH ACCOMMODATION

(75) Inventor: Robert E. Kellan, Andover, MA (US)

(73) Assignee: Anew Optics, Inc., Newton Centre, MA (US)

( * ) Notice: Subject to any disclaimer, the term of this patent is extended or adjusted under 35 U.S.C. 154(b) by 240 days.

(21) Appl. No.: 11/398,412

(22) Filed: Apr. 5, 2006

(65) Prior Publication Data

US 2007/0239274 A1 Oct. 11, 2007

(51) Int. Cl.
*A61F 2/16* (2006.01)
(52) U.S. Cl. ...................................... 623/6.43
(58) Field of Classification Search .................. 623/4.1, 623/6.11, 6.37–6.44, 6.46, 6.51, 6.52–6.54
See application file for complete search history.

(56) References Cited

U.S. PATENT DOCUMENTS

| | | | |
|---|---|---|---|
| 3,673,616 A | 7/1972 | Fedorov et al. | |
| 3,866,249 A | 2/1975 | Flom | |
| 3,906,551 A | 9/1975 | Otter | |
| 3,913,148 A | 10/1975 | Potthast | |
| 3,975,779 A | 8/1976 | Richards et al. | |
| 4,014,049 A | 3/1977 | Richards et al. | |
| 4,053,953 A | 10/1977 | Flom et al. | 623/6.38 |
| 4,073,014 A | 2/1978 | Poler | |
| 4,087,866 A | 5/1978 | Choyce et al. | |
| 4,092,743 A | 6/1978 | Kelman | |
| 4,102,567 A | 7/1978 | Cuffe et al. | |
| 4,136,406 A | 1/1979 | Norris | |
| 4,141,973 A | 2/1979 | Balazs | |
| 4,159,546 A | 7/1979 | Shearing | |
| 4,173,281 A | 11/1979 | Trought | |
| 4,174,543 A | 11/1979 | Kelman | |
| 4,190,049 A | 2/1980 | Hager et al. | |
| 4,198,980 A | 4/1980 | Clark | |
| 4,215,440 A | 8/1980 | Worst | |
| 4,240,163 A | 12/1980 | Galin | |
| 4,242,760 A | 1/1981 | Rainin | |
| 4,244,060 A | 1/1981 | Hoffer | |

(Continued)

FOREIGN PATENT DOCUMENTS

CN 1713862 12/2005
DE 2556665 6/1977

(Continued)

OTHER PUBLICATIONS

PCT Search Report for PCT/US2009/065955 dated May 31, 2011.

(Continued)

*Primary Examiner* — William H. Matthews
(74) *Attorney, Agent, or Firm* — Remenick PLLC

(57) ABSTRACT

An intraocular lens (IOL) assembly for correcting myopia, hyperopia and astigmatism is provided. The intraocular lens assembly comprises a lens extending along an optical axis between an anterior optical surface and a posterior optical surface. The IOL has a circumferential edge disposed about the optical axis at a junction of anterior and posterior optical surfaces with N haptics, where N is an integer greater than 1. Each haptic extends from an associated portion of the circumferential edge and along an associated haptic axis and extends between end portions joined to the lens at the circumferential edge. Each of the haptics includes M footplates extending symmetrically about its associated haptic axis, where M may be an integer greater than 0. The resultant vaulted structure provides an intraocular lens assembly that, when implanted in the eye, allows accommodation.

19 Claims, 7 Drawing Sheets

U.S. PATENT DOCUMENTS

| | | | |
|---|---|---|---|
| 4,249,271 A | 2/1981 | Poler | |
| 4,251,887 A | 2/1981 | Anis | |
| 4,254,509 A | 3/1981 | Tennant | 623/6.37 |
| 4,254,510 A | 3/1981 | Tennant | |
| 4,269,307 A | 5/1981 | LaHaye | |
| 4,270,230 A | 6/1981 | Poler | |
| 4,280,232 A | 7/1981 | Hummel | |
| 4,285,072 A | 8/1981 | Morcher et al. | 623/6.51 |
| 4,325,375 A | 4/1982 | Nevyas | |
| 4,326,306 A | 4/1982 | Poler | |
| 4,349,027 A | 9/1982 | DiFrancesco | |
| 4,363,142 A | 12/1982 | Meyer | |
| 4,363,143 A | 12/1982 | Callahan | |
| 4,366,582 A | 1/1983 | Faulkner | |
| 4,370,760 A | 2/1983 | Kelman | |
| 4,409,691 A | 10/1983 | Levy | |
| 4,423,809 A | 1/1984 | Mazzocco | |
| 4,435,855 A | 3/1984 | Pannu | |
| 4,441,217 A | 4/1984 | Cozean, Jr. | |
| 4,446,581 A | 5/1984 | Blake | |
| 4,451,938 A | 6/1984 | Kelman | |
| 4,463,458 A | 8/1984 | Seidner | |
| 4,468,820 A | 9/1984 | Uhler et al. | |
| 4,480,340 A | 11/1984 | Shepard | |
| 4,494,254 A | 1/1985 | Lopez | |
| 4,504,981 A | 3/1985 | Walman | |
| 4,508,216 A | 4/1985 | Kelman | |
| 4,517,295 A | 5/1985 | Bracke et al. | |
| 4,527,294 A | 7/1985 | Heslin | |
| 4,530,117 A | 7/1985 | Kelman | |
| 4,534,069 A | 8/1985 | Kelman | |
| 4,536,895 A | 8/1985 | Bittner | |
| 4,573,998 A | 3/1986 | Mazzocco | |
| 4,575,374 A | 3/1986 | Anis | |
| 4,576,607 A | 3/1986 | Kelman | |
| 4,581,033 A | 4/1986 | Callahan | |
| 4,585,456 A | 4/1986 | Blackmore | |
| 4,591,358 A | 5/1986 | Kelman | |
| 4,608,049 A | 8/1986 | Kelman | |
| 4,615,703 A | 10/1986 | Callahan et al. | |
| 4,619,256 A | 10/1986 | Horn | |
| 4,624,669 A | 11/1986 | Grendahl | |
| 4,629,460 A | 12/1986 | Dyer | |
| 4,634,423 A | 1/1987 | Bailey, Jr. | |
| 4,638,056 A | 1/1987 | Callahan et al. | |
| 4,655,775 A | 4/1987 | Clasby, III | |
| 4,676,792 A | 6/1987 | Praeger | 623/6.36 |
| 4,676,794 A | 6/1987 | Kelman | |
| 4,684,014 A | 8/1987 | Davenport | |
| 4,687,484 A | 8/1987 | Kaplan | |
| 4,700,638 A | 10/1987 | Przewalski | |
| 4,701,181 A | 10/1987 | Arnott | |
| 4,704,123 A * | 11/1987 | Smith | 623/6.43 |
| 4,710,195 A | 12/1987 | Giovinazzo | |
| 4,711,638 A | 12/1987 | Lindstrom | 623/6.54 |
| 4,718,906 A | 1/1988 | Mackool | |
| 4,736,836 A | 4/1988 | Alongi et al. | |
| 4,764,169 A | 8/1988 | Grendahl | |
| 4,769,035 A | 9/1988 | Kelman | |
| 4,778,464 A | 10/1988 | Sergienko et al. | |
| 4,781,719 A | 11/1988 | Kelman | |
| 4,787,902 A | 11/1988 | Sheets et al. | |
| 4,795,460 A | 1/1989 | Anis | |
| 4,795,462 A | 1/1989 | Grendahl | |
| 4,804,361 A | 2/1989 | Anis | |
| 4,816,032 A | 3/1989 | Hetland | 623/6.14 |
| 4,828,558 A | 5/1989 | Kelman | |
| 4,834,750 A | 5/1989 | Gupta | |
| 4,842,600 A | 6/1989 | Feaster | |
| RE33,039 E | 8/1989 | Arnott | |
| 4,852,566 A | 8/1989 | Callahan et al. | |
| 4,863,462 A | 9/1989 | Fedorov et al. | |
| 4,863,463 A | 9/1989 | Tjan | |
| 4,863,465 A | 9/1989 | Kelman | |
| 4,871,363 A | 10/1989 | Kelman | |
| 4,872,876 A | 10/1989 | Smith | |
| 4,878,911 A | 11/1989 | Anis | |
| 4,888,012 A | 12/1989 | Horn | |
| 4,919,130 A | 4/1990 | Stoy et al. | |
| 4,923,296 A | 5/1990 | Erickson | |
| 4,932,970 A | 6/1990 | Portney | |
| 4,950,290 A | 8/1990 | Kamerling | |
| 4,994,080 A | 2/1991 | Shepard | 623/6.64 |
| 4,995,714 A | 2/1991 | Cohen | |
| 5,002,568 A | 3/1991 | Katzen | |
| 5,019,098 A | 5/1991 | Mercier | |
| 5,047,052 A | 9/1991 | Dubroff | |
| 5,076,684 A | 12/1991 | Simpson et al. | |
| 5,092,880 A * | 3/1992 | Ohmi | 623/6.23 |
| 5,098,444 A | 3/1992 | Feaster | |
| 5,100,226 A | 3/1992 | Freeman | |
| 5,108,429 A | 4/1992 | Wiley | |
| 5,118,452 A | 6/1992 | Lindsey et al. | |
| 5,123,905 A | 6/1992 | Kelman | |
| 5,133,747 A | 7/1992 | Feaster | 623/6.34 |
| 5,133,749 A | 7/1992 | Nordan | |
| 5,166,711 A | 11/1992 | Portney | |
| 5,171,320 A | 12/1992 | Nishi | |
| 5,176,686 A | 1/1993 | Poley | |
| 5,178,636 A | 1/1993 | Silberman | |
| 5,192,319 A | 3/1993 | Worst | |
| 5,197,981 A | 3/1993 | Southard | |
| 5,199,559 A | 4/1993 | Dark | |
| 5,229,797 A | 7/1993 | Futhey et al. | |
| 5,236,452 A | 8/1993 | Nordan | |
| 5,258,025 A | 11/1993 | Fedorov et al. | |
| 5,266,074 A | 11/1993 | Nishi et al. | |
| 5,281,227 A | 1/1994 | Sussman | |
| 5,361,780 A | 11/1994 | Kellan | |
| 5,366,501 A | 11/1994 | Langerman | |
| 5,370,652 A | 12/1994 | Kellan | |
| 5,405,386 A | 4/1995 | Rheinish et al. | |
| 5,425,734 A | 6/1995 | Blake | |
| D360,068 S | 7/1995 | Hambleton et al. | |
| 5,443,506 A | 8/1995 | Garabet | |
| 5,468,246 A | 11/1995 | Blake | |
| 5,476,512 A | 12/1995 | Sarfarazi | |
| 5,476,514 A | 12/1995 | Cumming | |
| 5,480,428 A | 1/1996 | Fedorov et al. | |
| 5,489,302 A | 2/1996 | Skottun | |
| 5,496,366 A | 3/1996 | Cumming | |
| 5,507,806 A | 4/1996 | Blake | |
| 5,522,890 A | 6/1996 | Nakajima et al. | |
| 5,549,670 A | 8/1996 | Young et al. | |
| 5,593,436 A | 1/1997 | Langerman | |
| 5,628,794 A | 5/1997 | Lindstrom | |
| 5,643,275 A | 7/1997 | Blake | |
| D382,399 S | 8/1997 | Hambleton et al. | |
| 5,674,282 A | 10/1997 | Cumming | |
| 5,682,223 A | 10/1997 | Menezes et al. | |
| 5,697,973 A | 12/1997 | Peyman | |
| 5,709,220 A | 1/1998 | Kellan | |
| 5,713,958 A | 2/1998 | Weiser | |
| 5,772,667 A | 6/1998 | Blake | |
| 5,782,911 A | 7/1998 | Herrick | |
| 5,800,532 A | 9/1998 | Lieberman | |
| 5,847,802 A | 12/1998 | Menezes et al. | |
| 5,855,605 A | 1/1999 | Herrick | |
| 5,919,229 A | 7/1999 | Portney | |
| 5,928,282 A | 7/1999 | Nigam | 623/6.43 |
| 5,947,976 A | 9/1999 | Van Noy et al. | |
| 5,976,150 A | 11/1999 | Copeland | |
| 6,010,510 A | 1/2000 | Brown | |
| 6,013,101 A | 1/2000 | Israel | |
| 6,015,435 A | 1/2000 | Valunin et al. | 623/6.28 |
| 6,051,024 A | 4/2000 | Cumming | |
| 6,083,261 A | 7/2000 | Callahan et al. | 623/6.38 |
| 6,090,141 A | 7/2000 | Lindstrom | |
| 6,096,077 A | 8/2000 | Callahan et al. | |
| 6,110,202 A | 8/2000 | Barraquer et al. | |
| 6,120,148 A | 9/2000 | Fiala et al. | |
| 6,129,723 A | 10/2000 | Anderson | |
| 6,142,999 A | 11/2000 | Brady et al. | 606/106 |
| 6,152,958 A | 11/2000 | Nordan | |
| 6,197,059 B1 | 3/2001 | Cumming | |
| 6,203,549 B1 | 3/2001 | Waldock | |
| 6,224,628 B1 | 5/2001 | Callahan et al. | |

| | | | | | | |
|---|---|---|---|---|---|---|
| 6,241,777 B1 | 6/2001 | Kellan ......... 623/6.51 | | 2011/0191086 A1 | 8/2011 | Callahan |
| 6,261,321 B1 | 7/2001 | Kellan | | 2011/0313522 A1 | 12/2011 | Hayes |
| 6,277,146 B1 | 8/2001 | Peyman et al. | | 2011/0313523 A1 | 12/2011 | Hayes |

FOREIGN PATENT DOCUMENTS

| | | |
|---|---|---|
| DE | 2717706 | 10/1978 |
| DE | 3722910 | 1/1989 |
| DE | 4030005 | 3/1992 |
| DE | 4040005 | 6/1992 |
| EP | 1961399 | 4/1991 |
| FR | 2653325 | 4/1991 |
| FR | 2666503 | 3/1992 |
| FR | 2687304 | 8/1993 |
| GB | 2029235 | 3/1980 |
| GB | 2124500 | 2/1984 |
| GB | 2165456 | 4/1986 |
| SU | 1377086 | 2/1988 |
| WO | WO 98/17205 | 4/1998 |
| WO | WO 99/29266 | 6/1999 |
| WO | WO00/78252 | 12/2000 |
| WO | WO03017867 | 6/2003 |
| WO | WO 2007117476 | 10/2007 |
| WO | WO 2007134019 | 11/2007 |

OTHER PUBLICATIONS

| | | |
|---|---|---|
| 6,299,641 B1 | 10/2001 | Woods |
| 6,398,786 B1 | 6/2002 | Sesic |
| 6,443,985 B1 | 9/2002 | Woods |
| 6,447,519 B1 | 9/2002 | Brady |
| 6,461,384 B1 | 10/2002 | Hoffmann |
| 6,488,707 B1 | 12/2002 | Callahan et al. |
| 6,488,709 B1 | 12/2002 | Barrett |
| 6,494,911 B2 * | 12/2002 | Cumming ......... 623/6.37 |
| 6,517,577 B1 | 2/2003 | Callahan et al. |
| 6,533,813 B1 | 3/2003 | Lin et al. |
| 6,537,283 B2 | 3/2003 | Van Noy |
| 6,605,093 B1 | 8/2003 | Blake |
| 6,622,855 B1 | 9/2003 | Callahan et al. |
| 6,623,522 B2 | 9/2003 | Nigam |
| 6,645,246 B1 | 11/2003 | Weinschenk, III |
| 6,666,887 B1 | 12/2003 | Callahan et al. |
| 6,749,633 B1 | 6/2004 | Lorenzo |
| 6,786,928 B2 | 9/2004 | Callahan et al. |
| 6,797,004 B1 | 9/2004 | Brady |
| 6,800,091 B2 | 10/2004 | Callahan et al. |
| 6,921,415 B2 | 7/2005 | Callahan et al. |
| 6,976,989 B1 | 12/2005 | Vincent |
| 7,037,328 B2 | 5/2006 | Vincent |
| 7,037,338 B2 | 5/2006 | Nagamoto |
| 7,063,723 B2 | 6/2006 | Ran |
| 7,125,422 B2 | 10/2006 | Woods |
| 7,179,292 B2 | 2/2007 | Worst |
| 7,220,279 B2 | 5/2007 | Nun |
| 7,223,288 B2 | 5/2007 | Zhang |
| 7,279,006 B2 | 10/2007 | Vincent |
| 7,354,451 B2 | 4/2008 | Koch |
| 7,503,938 B2 | 3/2009 | Phillips |
| 7,713,299 B2 | 5/2010 | Brady et al. |
| 8,043,372 B2 | 10/2011 | Bumbalough |
| 2001/0012964 A1 | 8/2001 | Lang |
| 2001/0044657 A1 | 11/2001 | Kellan |
| 2001/0044857 A1 | 11/2001 | Pham et al. |
| 2002/0055777 A1 | 5/2002 | Cumming et al. |
| 2002/0072673 A1 | 6/2002 | Yamamoto |
| 2002/0095212 A1 | 7/2002 | Boehm |
| 2002/0103536 A1 | 8/2002 | Landreville et al. |
| 2002/0120331 A1 | 8/2002 | Galin et al. |
| 2002/0161437 A1 | 10/2002 | Zhou et al. |
| 2002/0193877 A1 | 12/2002 | Hoffmann et al. |
| 2003/0033013 A1 | 2/2003 | Callahan |
| 2003/0050695 A1 | 3/2003 | Lin et al. |
| 2003/0065387 A1 | 4/2003 | Callahan et al. |
| 2003/0078655 A1 | 4/2003 | Callahan |
| 2003/0114927 A1 | 6/2003 | Nagamoto |
| 2003/0130732 A1 * | 7/2003 | Sarfarazi ......... 623/6.13 |
| 2003/0135273 A1 | 7/2003 | Callahan |
| 2003/0149480 A1 | 8/2003 | Shadduck et al. |
| 2004/0215340 A1 | 10/2004 | Messner et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0033308 A1 | 2/2005 | Callahan |
| 2005/0107875 A1 | 5/2005 | Cumming |
| 2005/0251253 A1 | 11/2005 | Gross |
| 2006/0047339 A1 | 3/2006 | Brown |
| 2006/0047340 A1 | 3/2006 | Brown |
| 2006/0100704 A1 | 5/2006 | Blake |
| 2006/0142781 A1 | 6/2006 | Pynson et al. |
| 2006/0235515 A1 | 10/2006 | Chassain |
| 2006/0247767 A1 | 11/2006 | Koch |
| 2006/0293694 A1 | 12/2006 | Futamura |
| 2007/0093892 A1 | 4/2007 | Mackool |
| 2007/0239274 A1 | 10/2007 | Kellan |
| 2008/0161913 A1 | 7/2008 | Brady et al. |
| 2008/0281417 A1 | 11/2008 | Nagamoto |
| 2009/0171458 A1 | 7/2009 | Kellan et al. |
| 2009/0248031 A1 | 10/2009 | Ichinohe et al. |
| 2010/0131059 A1 | 5/2010 | Callahan et al. |
| 2010/0131061 A1 | 5/2010 | Callahan et al. |
| 2010/0179652 A1 | 7/2010 | Yamamoto |
| 2010/0228260 A1 | 9/2010 | Callahan et al. |

PCT Patentability Report for PCT/US2009/065955 dated Jan. 27, 2010.
PCT Search Report for PCT/US2009/065960 dated Jan. 27, 2010.
PCT Patentability Report for PCT/US2009/065960 dated Jan. 27, 2010.
PCT Search Report for PCT/US2007/008328 dated Jun. 19, 2008.
PCT Patentability Report for PCT/US2007/008328 dated Jun. 19, 2008.
PCT Search Report for PCT/US2008/088430 dated Aug. 11, 2009.
PCT Patentability Report for PCT/US2008/088430 dated Aug. 11, 2009.
PCT Search Report for PCT/US2010/026230 dated May 19, 2010.
PCT Patentabilty Report for PCT/US2010/026230 dated May 19, 2010.
PCT Search Report for PCT/US2006/16221 dated May 10, 2007.
PCT Patentability Report for PCT/US2006/16221 dated May 10, 2007.
PCT Search Report for PCT/US2011/37583 dated Nov. 15, 2011.
PCT Patentabilty Report for PCT/US2011/37583 dated Nov. 15, 2011.
Chinese First Office Action dated Aug. 27, 2011.
Zaldivar et al,; "The Current Status of Phakic Intraocular Lenses;" International Opthamology Clinics; vol. 36, No. 4; 1996; pp. 107-111.
Neuhann; "Corneal or Lens Refractive Surgery?" Journal of Refractive Surgery; vol. 14; May/Jun. 1998; pp. 272-279.
Rosen et al.; "Staar Collamer Posterior Chamber Phakic Intraocular Lens to Correct Myopia and Hyperopia;" J. Cataract Refract. Surg.; vol. 24; May 1998; pp. 596-606.
Sanders et al; "Implantable Contact Lens for Moderate to High Myopia: Phase 1 FDA Clinical Study with 6 Month Follow-Up;" J. Cataract Refract Surg.; vol. 24; May 1998; pp. 607-6111.
PCT Search Report of Jan. 27, 2010.
PCT Patentability Report of Jan. 27, 2010.
PCT Search Report of May 19, 2010.
PCT Patentability Report of May 19, 2010.
Chinese Office Action of Apr. 12, 2011 with uncertified English translation.
Chinese Office Action for Chinese Application 200780020967.4 dated Apr. 12, 2011.
Austria Examination Report for Austrian Application 200807369-4 dated Mar. 10, 2010.
Japan Office Action for Japanese Application 2009-504268, dated Apr. 24, 2012.
Chinese Decision of Rejection for Chinese Application 200780020967.4, dated May 28, 2012.
Austria Examination Report for Austrian Application 2009319753, dated Aug. 29, 2012.

PCT Search Report and Patentability Report for PCT/US12/40732, dated Sep. 18, 2012.

EPO Search Report for PCT/US2007/008328, dated Oct. 26, 2012.

EPO Opinion for PCT/US2007/008328, dated Oct. 26, 2012.

* cited by examiner

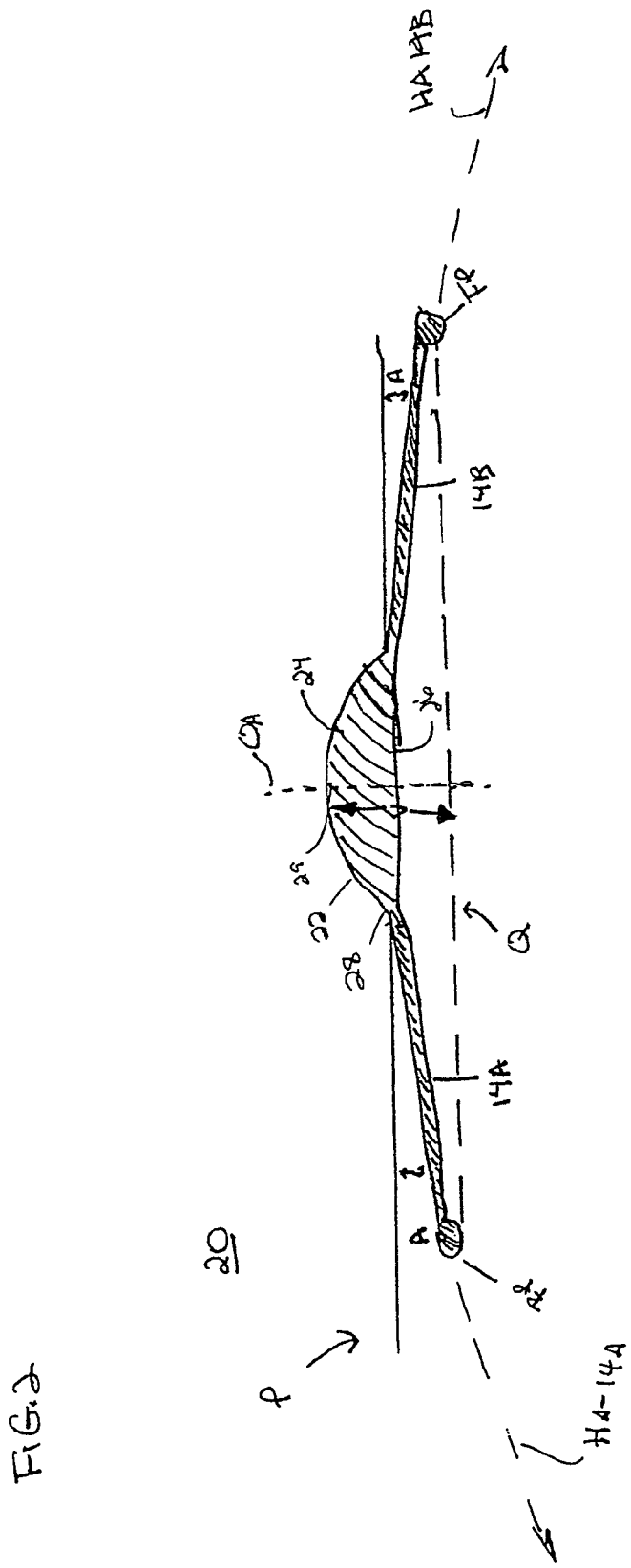

INTRAOCULAR LENS WITH ACCOMMODATION

TECHNICAL FIELD

The present invention relates to implantable intraocular lenses ("IOL") suitable for the correction of myopia, hyperopia, and astigmatism. More particularly, the invention relates to IOLs which are adapted to provide accommodation.

BACKGROUND ART

Implantation of artificial lenses into the human eye has been a standard technique for many years, both to replace the natural crystalline lens (aphakic eye) and to supplement and correct refractive errors of the natural lens (phakic eye). However, accommodation provided by such replacement lenses is minimal or non-existent.

The human eye includes an anterior chamber between the cornea and iris, a posterior chamber, defined by a capsular bag containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL provides very limited, if any, accommodation. However, the wearer of such an IOL continues to require the ability to view both near and distant objects. Corrective spectacles may be employed as a useful solution. Recently, multifocal IOLs, defractive or refractive, divide light entering the eye and have been used to provide near and distant vision correction. Though they do provide some accommodation, they decrease contrast sensitivity and cause photopic problems such as glare and halos.

Examples of implantable intraocular lenses include various design configurations without providing significant accommodation. Generally, the lenses are attached in some manner to the eye, usually by the use of sutures or some other supporting means, such as arms or haptics, extending from the optical lens portion of the intraocular lens.

U.S. Pat. No. 6,241,777 describes a phakic intraocular lens assembly that has a lens with a circumferential edge, and a first haptic and a second haptic, which extend from the edge of the lens. Each of the haptics has a first leg extending from the lens edge to a distal end, and a second leg extending from the lens edge to a distal end, and a transverse member extending between the distal ends of each first and second leg. The transverse member can be substantially straight or bowed inward toward the lens. Each leg has a footplate at its distal end.

U.S. Pat. No. 6,261,321 (Continuation-in-part of U.S. Pat. No. 6,241,777) describes a phakic or aphakic intraocular lens assembly that has a lens with a circumferential edge, and a first haptic and a second haptic, which extend from the edge of the lens. Each of the haptics has a first leg extending from the lens edge to a distal end, and a second leg extending from the lens edge to a distal end, and a transverse member extending between the distal ends of each first and second leg. The transverse member can be substantially straight or bowed inward toward the lens. Each leg has a footplate at its distal end. Each leg of each haptic may be inwardly bowing, straight, and outwardly bowing. Additionally, each leg may have the same or different shape from the other legs.

U.S. Pat. No. 6,015,435 describes a self-centering phakic intraocular lens inserted in to the posterior chamber lens for the correction of myopia, hyperopia, astigmatism, and presbyopia. Haptic bodies are attached to optical body and extend outward from tangent points at the edge of lens in at least two generally opposite directions. Protruding surfaces protrude into pupil such that the iris interferes slightly with lens movement and provides the centering force to keep lens in place.

U.S. Pat. No. 5,133,747 describes an intraocular lens device that is partially or completely within the anterior capsular surface of the human crystalline lens. In one embodiment, the optic body has asymmetrical haptics extending outwardly from opposite sides of the circumferential edge of the optic body. In one embodiment, "J" shaped haptics extend from the circumferential edge of the optic body in a manner that encircles optic body. In another configuration, the haptics extend tangentially away from body, then reverse direction, giving the device an overall "S" shape with the lens at center portion of the S. The device is secured in place with an adhesive.

Attempts have been made to provide IOLs with accommodation, using movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. These lenses are biased to be located in the posteriormost position in the eye under rest or resting conditions. When near focus is desired, the ciliary muscle contracts and the lens moves forwardly (positive accommodation). In the absence of ciliary muscle contraction, the lens moves rearward to its posterior-most resting position. Because of this posterior bias and the configuration of the lens, the posterior wall of the capsular bag is subjected to a substantial degree of stretching when the lens is in the posterior-most position. One problem that exists with such IOLs is that they often cannot move sufficiently to obtain the desired accommodation.

Therefore, it would be advantageous to provide IOLs which can achieve an acceptable amount of accommodation with reduced risk of damaging the capsular bag.

SUMMARY OF THE INVENTION

An intraocular lens (IOL) assembly and method for correcting myopia, hyperopia and astigmatism using the intraocular lens assembly are provided. In particular, the intraocular lens assembly relates to intraocular lenses which provide accommodation. The intraocular lens assembly comprises a lens extending along an optical axis between an anterior optical surface and a posterior optical surface. The lens has a circumferential edge disposed about the optical axis at a junction of anterior and posterior optical surfaces. The lens further has N haptics, where N is an integer greater than 1. Furthermore, each haptic extends from an associated portion of the circumferential edge and along an associated haptic axis. In addition, each haptic is "loop-like" or "paddle-like" and extends between end portions at opposite ends thereof joined to the lens at the circumferential edge. It should be noted that each of the haptics may include M footplates extending symmetrically about its associated haptic axis, where M is an integer greater than 0. Alternatively, each of the haptics may not include any footplates.

In one embodiment of the present invention, an intraocular lens assembly may include a first pair of haptics extending from opposite portions of circumferential edge along an associated first pair of haptic axes, and having a second pair of haptics extending from opposite portions of circumferential edge along an associated second pair of haptic axes, wherein first pair of haptic axes and optic axis are coplanar in a first haptic plane wherein second pair of haptic axes and optic axis are coplanar in a second haptic plane. In addition, the first haptic plane may be perpendicular to second haptic plane, although angle arrangements other than perpendicular may be used in other forms of the invention. The haptics are angularly displaced with respect to optical axis in a direction away from the anterior optical surface by an angle A from a plane P transverse to optical axis. In an embodiment, an intraocular lens assembly can have an angle A with an approximate range of 4-7 degrees. It should also be noted that each haptic may include at least one footplate extending therefrom symmetrically about its associated haptic axis. Alternatively, each of the haptics may not include any footplates.

The invention also provides a method for implanting in an eye an intraocular lens assembly which provides accommodation. This includes the insertion of an intraocular lens (IOL) assembly into the eye, where the IOL assembly extends along an optical axis between an anterior optical surface and a posterior optical surface. The lens of the IOL has a circumferential edge disposed about an optical axis at a junction of the anterior and posterior optical surfaces. The lens further includes N haptics, where N is an integer greater than 1. Each haptic extends from an associated portion of the circumferential edge and along an associated haptic axis. Each of the haptics is "loop-like" or "paddle-like" and extends between end portions at opposite ends thereof. The end portions are joined to the lens at the circumferential edge. Also, the haptic axis is angulated away from anterior surface by angle A with respect to a plane P transverse to the optical axis. In one embodiment, angle A may be in an approximate range of 4-7 degrees.

BRIEF DESCRIPTION OF THE DRAWINGS

The invention, and the various features thereof, may be more fully understood from the following description, when read together with the accompanying drawings, in which:

FIG. 2 shows a cross sectional view of the lens assembly of FIG. 1 along axis A.

DETAILED DESCRIPTION OF THE INVENTION

In the eye, the natural lens of the eye separates the aqueous humor from the vitreous body. The iris separates the region between the cornea or anterior of the eye and the lens into an anterior chamber and a posterior chamber. The natural crystalline lens is contained in a membrane known as the capsule or capsular sac. When the natural lens is removed from the eye, the capsule may also be removed (intracapsular excision), or the anterior portion of the capsule may be removed with the natural crystalline lens, leaving the posterior portion of the capsule intact (extracapsular extraction), often leaving small folds or flaps from the anterior portion of the capsule. In an intraocular implant, an artificial lens may be inserted in the anterior chamber, the posterior chamber, or the capsular sac.

The design of intraocular lens assembly of the present invention and particularly the loop-like or paddle-like, flexible haptics, preferably with angulation, overcomes the lack of accommodation provided by prior intraocular devices. The intraocular lens assembly of the invention is primarily designed for placement in the anterior chamber of the eye and use as a refractive lens for the phakic eye. However, the unique design of the intraocular lens assembly also permits its use in the aphakic eye, and placement in the posterior chamber sulcus and the posterior chamber bag. The intraocular lens assembly described herein is suitable for correction of myopia, hyperopia, and astigmatism without compromising the anatomy or physiology of the eye.

The intraocular lens assembly of the invention is made from a biocompatible, flexible material. In one embodiment, the material is also a foldable material, which allows insertion of the device through small incisions, usually 3 mm or less. Since the device is preferably inserted into the anterior chamber of the eye, there is no contact with the natural crystalline lens, so that cataract formation is minimized. The design provides minimal contact with other tissues in the eye. Furthermore, the device can be easily removed and reinserted as needed. The combination of flexible materials and the haptic design allows the device to withstand some deforming forces, such as the patient rubbing his eyes, without the device breaking, warping, or becoming disengaged from the eye.

Figure 1:
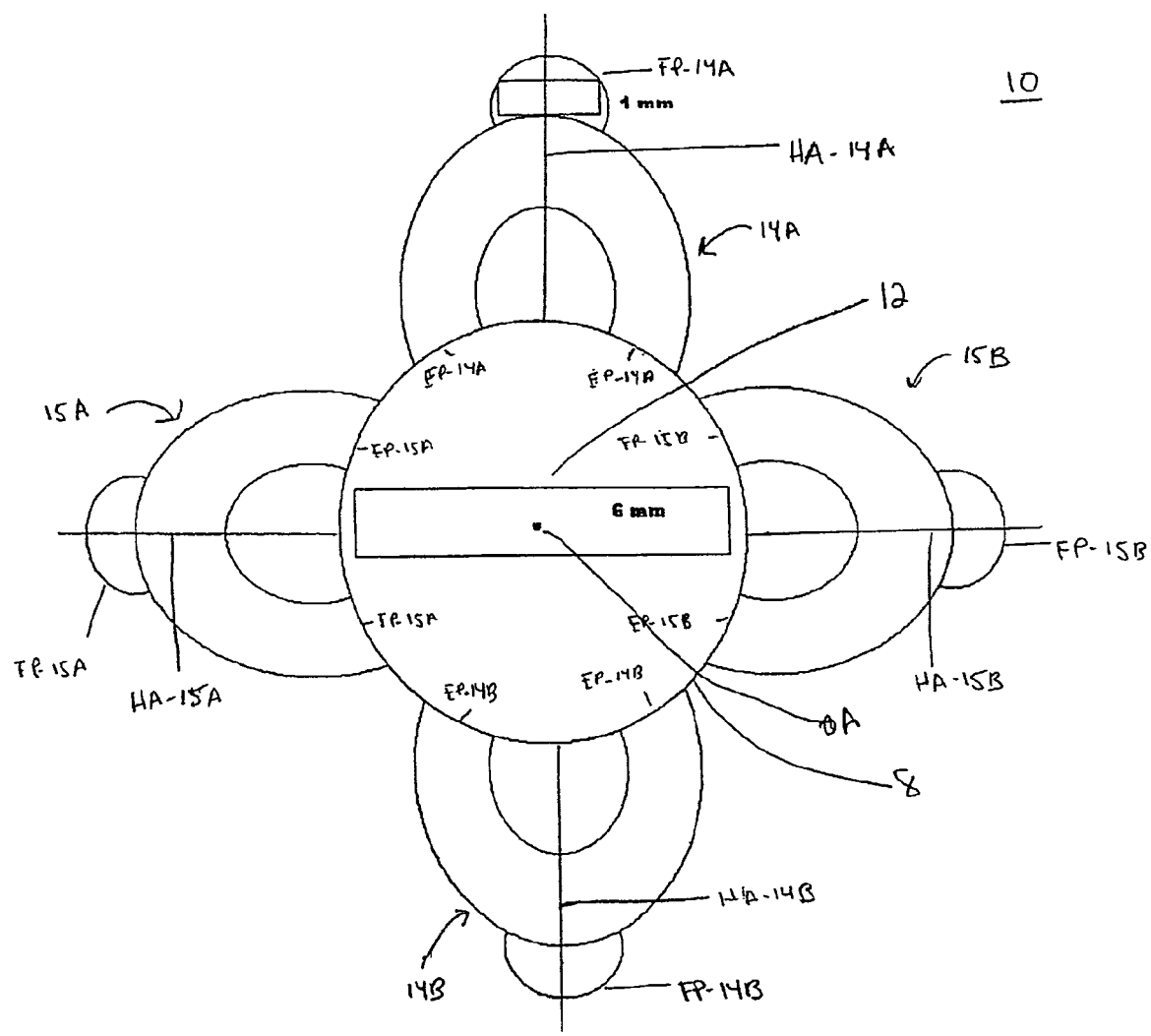
FIGS. 1 and 1A show a top view and a perspective view of the lens assembly of an embodiment of the present invention.

In one embodiment of the present invention, as illustrated in FIG. 1, an intraocular lens assembly 10 includes a lens portion (the "optic") 12 extending along an optical axis OA between an anterior optical surface and a posterior optical surface. The lens 12 of the IOL has a circumferential edge 8 (disposed about the optical axis OA) at a junction of anterior and posterior optical surfaces. The lens 12 has two pairs of opposed, flexible haptics 14A, 14B, and 15A, 15B extending from circumferential edge 8 of optic 12. The haptics extend along an associated haptic axis HA: haptic 14A extends along haptic axis HA-14A, haptic 14B extends along haptic axis HA-14B, haptic 15A extends along haptic axis HA-15A and haptic 15B extends along haptic axis HA-15B. In the illustrated embodiment, each haptic axis HA is coplanar with optical axis OA in an associated haptic plane. In other embodiments, a different number of haptics may be employed. For example there may be N haptics, where N is an integer.

Each of the flexible, haptics 14A, 14B, 15A and 15B are flexible and "loop-like" or "paddle-like". As used here, the term "loop-like" refers to a smooth, curved portion of a loop, for example, having a "C-shaped" or U-shaped peripheral edge, with uniform or non-uniform width. As used herein, the term "paddle-like" refers to a solid element (without a central aperture) bounded by a C-shaped or U-shaped peripheral edge. The haptics extend between end portions thereof which are joined to lens 12 at associated portions of circumferential edge 8. For example, haptic 14A extends between EP-14A and EP-14B, extending along haptic axis, HA-14A.

In the illustrated embodiments of FIG. 1, two pairs of opposed, flexible, loop-like haptics are spaced equidistant around circumferential edge 8 of optic 12. This symmetry provides the comfort to the patient and stability of the lens. Alternatively, two or more loop-like, flexible haptics may be attached at differently spaced, non-equidistant points or asymmetrically on a circumferential edge 8 extending along haptic axis HA, see FIGS. 5D-5G. In addition, two or more flexible haptics may be attached, depending upon the individual eye anatomy or vision requirements, to maximize accommodation and stability of the lens assembly.

Figure 1A:
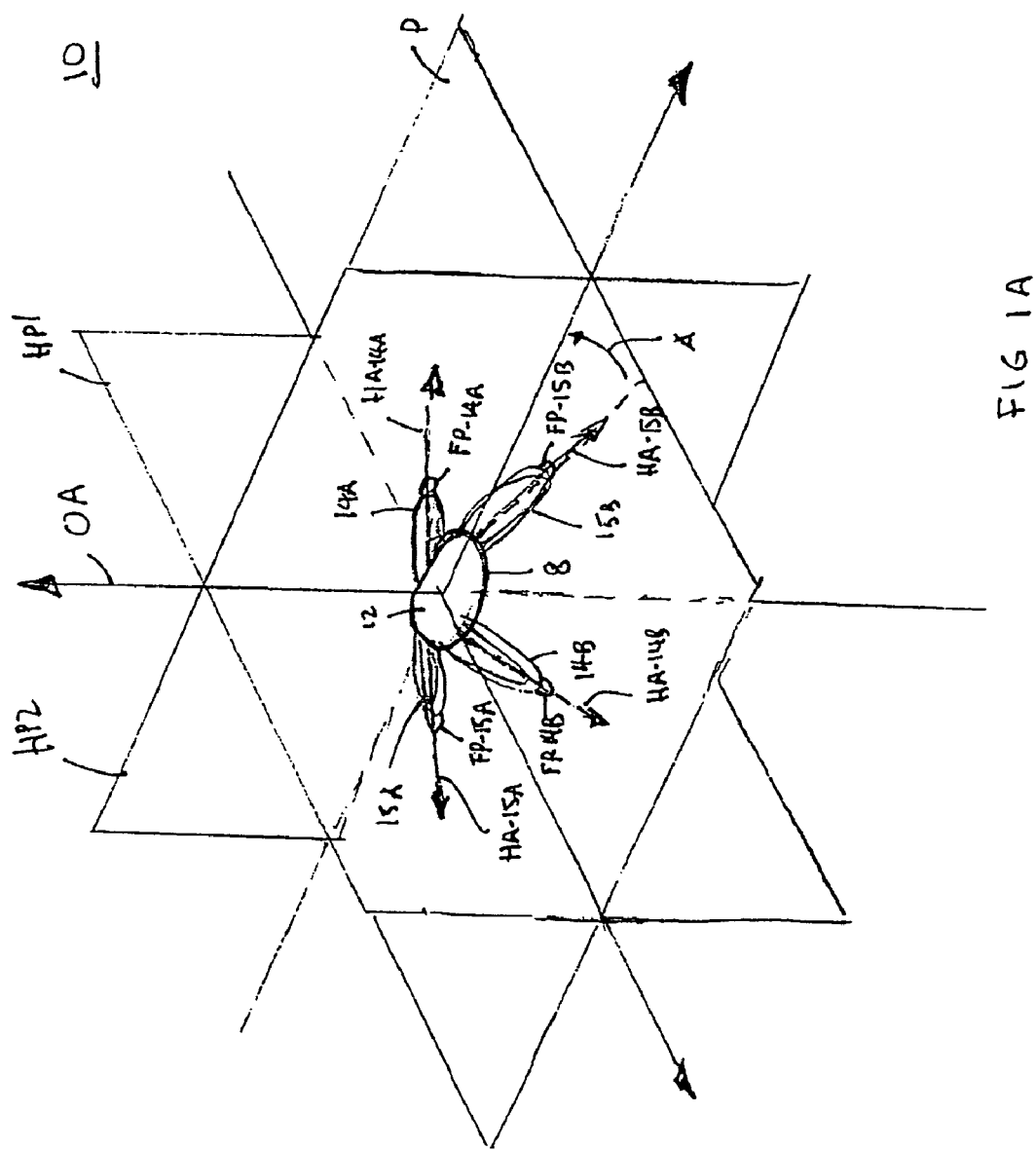

As shown in FIG. 1A, the intraocular lens assembly 10 includes a first pair of haptics 14A, 14B extending from opposite portions of circumferential edge 8 (in a plane P) along an associated first pair of haptic axes HA-14A, HA-14B and a second pair of haptics 15A, 15B extending from opposite portions of circumferential edge 8 along an associated second pair of haptic axes HA-15A, HA-15B, wherein first pair of haptic axes and optic axis OA are coplanar in a first haptic plane HP1 and wherein second pair of haptic axes and optic axis OA are coplanar in a second haptic plane HP2. In addition, the first haptic plane HP1 is perpendicular to second haptic plane HP2. The haptics are angularly displaced with respect to optical axis in a direction away from anterior optical surface by an angle A from the plane P transverse to optical axis OA. Preferably, the intraocular lens assembly uses an angle A with an approximate range of 4-7 degrees. It should also be noted that each haptic includes at least one footplate FP extending therefrom symmetrically about its associated haptic axis HA. Alternatively, each of the haptics may not include any footplates extending symmetrically about its associated haptic axis.

Figure 5C:
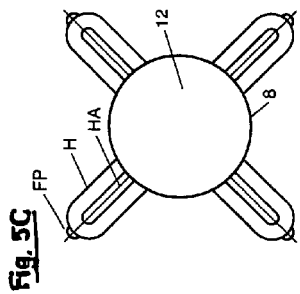
FIGS. 5A-5I show top views of alternative embodiments of lens assemblies of the present invention, with examples of haptic placement along a circumferential edge of a lens.
Figure 5F:
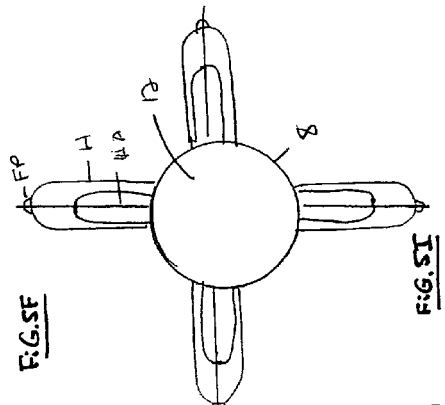
Figure 5I:
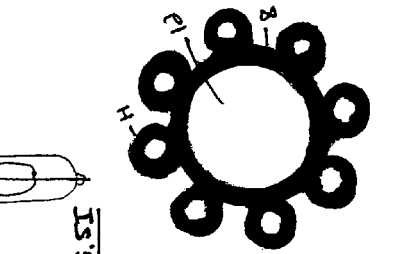
Figure 5B:
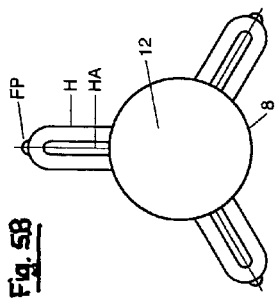
Figure 5E:
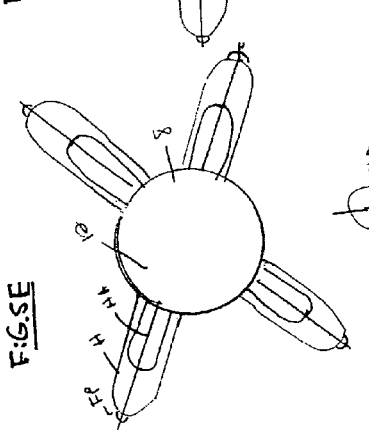
Figure 5H:
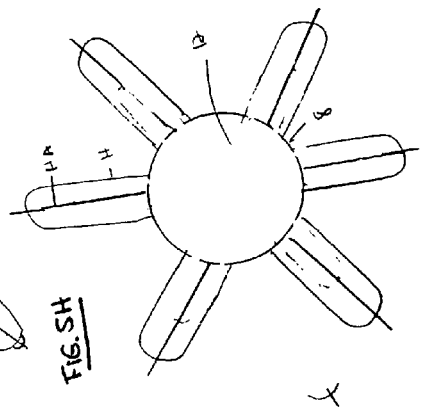
Figure 5A:
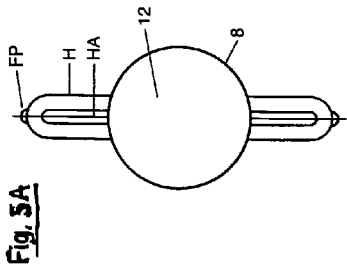
Figure 5D:
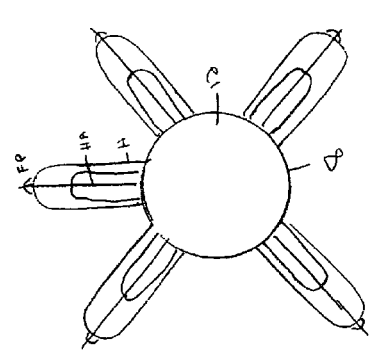
Figure 5G:

Each haptic includes M footplates FP extending symmetrically about its associated haptic axis HA, where M is an integer greater than 0. In one embodiment, M equals 1. Alternatively, each of the haptics may not include any footplates. In FIGS. 1 and 1A, the footplates FP are integrally formed on the distal end of each haptic HA, preferably at the apex of the haptic. As illustrated in FIG. 1, each haptic 14A, 14B, 15A, and 15B includes an associated one of footplates FP-14A, FP-14B, FP-15A, and FP-15B disposed symmetrically about its associated haptic axis HA-14A, HA-14B, HA-15A, and HA-15B. In other embodiments, there may be multiple footplates symmetrically disposed about the associated haptic axis. By way of example, various footplate configurations are shown in FIGS. 5A-5I. Note, in one embodiment, the configurations may not have any footplates. It should also be noted that footplates FP are preferably lenticular-shaped in cross-section to allow for minimal contact with the eye structures yet provide the required stability for the desired visual results. FIGS. 5A-5E and 5I show loop-like haptics, where FIGS. 5A-5C show uniform width haptics and FIGS. 5D-5G show non-uniform width haptics. FIG. 5H shows paddle-like haptics.

FIG. 2 shows an intraocular lens assembly, similar to intraocular lens assembly 10 of FIG. 1, along plane HP1 defined by optical axis OA and haptic axis HA-14A and HA-14B. Optic 22 constitutes the optical portion of the lens assembly. The optic 22 comprises an anterior optical surface 24 and posterior optical surface 26. The combination of surface 24 and surface 26 may result in the optic being substantially planar, convex, plano-convex (illustrated in FIG. 2) and concave, bi-convex, concave-convex, or other known form. The diameter of optic 22 can vary as needed to accommodate the angle-to-angle measurement of the eye and curvature of the eye. The overall length of the intraocular lens (optic and haptics) to be inserted into an individual patient's eye is determined by adding a 1 mm white-to-white measurement of the patient's eye. In one embodiment, Optic 22 has a 6 mm optical zone.

Optic 22 may be ground to the required diopter measurements necessary for vision correction. The lens may be a negative or positive meniscus lens and may include correction for astigmatism. Depending on the refractive index of the material used, and the required vision correction, optic 22 may have the same thickness at central portion 27 and circumferential edge 28, or central portion 27 may be thinner than circumferential edge 28. In one embodiment, the thickness of optic 22 is 1 mm.

In another embodiment, still referring to FIG. 2, flexible haptics 14A and 14B extend from circumferential edge 28 of optic 22 at a slight angle A from a plane P transverse to the optical axis OA. Vault distance V for assembly 20 is defined as the height of the lens assembly measured from a line Q, which is drawn horizontally (as shown) between footplates FP, to the apex 29 of inner optical surface 24 and along the optical axis OA. Angle A is in the approximate range 4 to 7 degrees, or more, as desired, to maximize accommodation of lens assembly 20. Preferably angle A is one that, when in combination with the size and shape of the optic and the flexible haptics and the assembly 20, and the anatomical angle of the eye, provides a 1 mm vault distance V, although other vault distances can be used. The vault distance insures adequate clearance for the intraocular lens assembly to be situated between the natural crystalline lens and the cornea in the anterior chamber.

Figure 3:
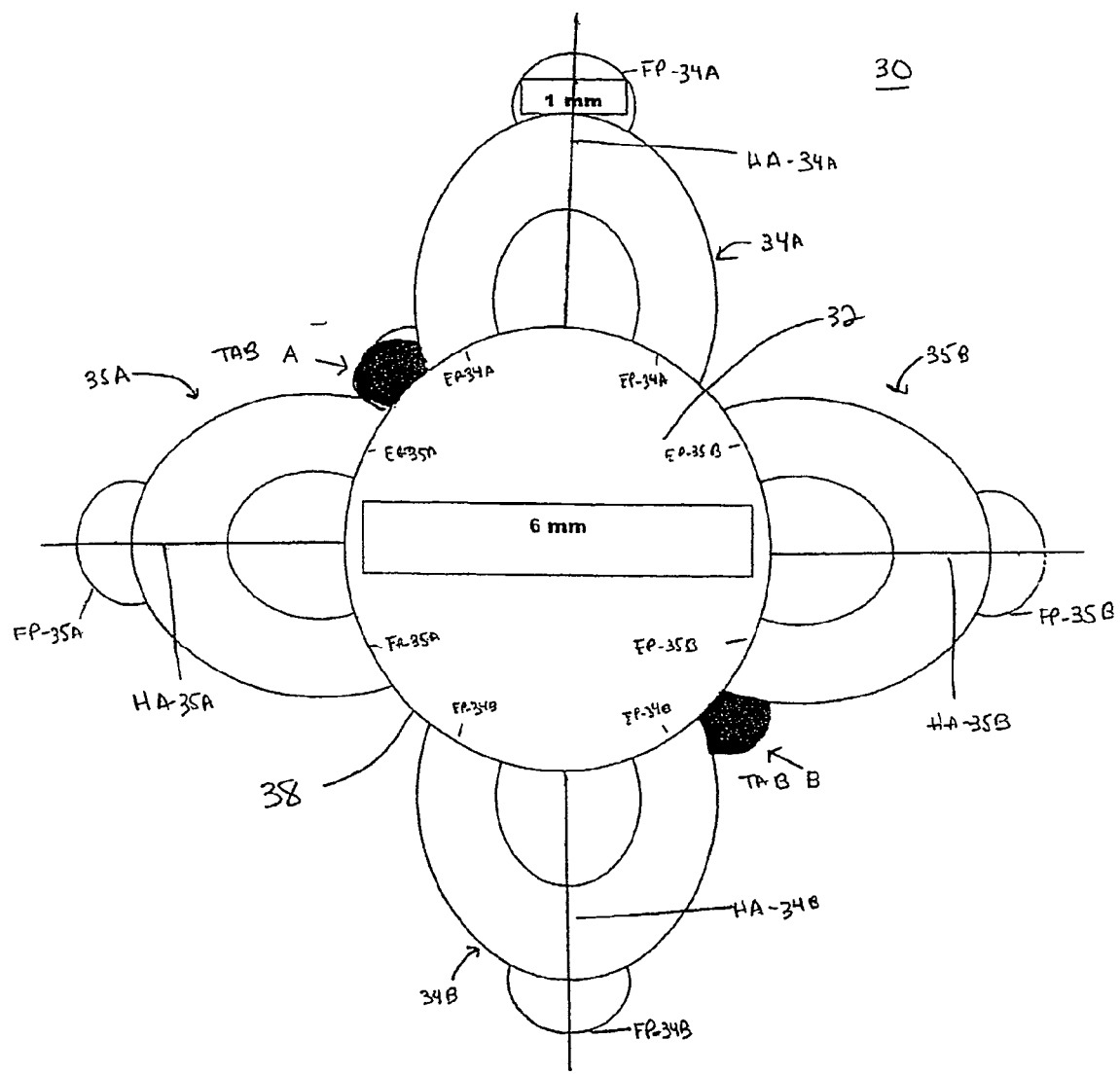
FIG. 3 shows a top view of an alternative embodiment of the lens assembly with orientation tabs.

As illustrated in FIG. 3, there is shown an intraocular lens assembly, similar to intraocular lens assembly 10 in FIG. 1, that includes a tab A and a tab B, extending from the circumferential edge 38 of optic 32. Those tabs assist the user (surgeon) in the identification of orientation of the lens assembly during implantation. The "left diagonal" orientation of the tabs is shown in FIG. 3, as viewed by the surgeon, indicate that the lens assembly is correctly implanted, with the lens being vaulted-forward. A right-diagonal orientation of tabs A and B would indicate that lens assembly 30 has been implanted in a backwards or reversed manner.

The preferred embodiment intraocular lens assembly of the invention is designed to be foldable to facilitate insertion through small incisions, generally 3 mm in length or less. The device can be folded along axis A, transverse to axis A, at an angle offset from axis A, or in multiple directions. The device can be folded in the optic body, at any point in the flexible haptics, at the junction points between the optic body and the flexible haptics, or all of the above. The device can be folded with single or multiple folds along each direction.

Suitable materials for the lens assembly of the invention are solid, flexible, foldable optical, non-biodegradable materials such as hydrogel, collamer, collagel (hydrogel-collagen blends) acrylic polymers, polymethylmethacrylate (PMMA) and silicone polymers. The lens assembly may also be made of a composite of materials, i.e. where the flexible haptics are fabricated from one material and the optics from another material, for example, acrylic optics and hydrogel haptics. Where the lens assembly is used in the aphakic eye, flexible, but less foldable, materials may be preferred. For example, for the aphakic eye, the lens assembly may be made of all PMMA or a composite of PMMA optics and prolene haptics.

By way of example, the lens assembly may be made as a sterile UV-absorbing acrylic foldable form, for example using the same material as the AcrySof™ IOL manufactured by Alcon Laboratories, Inc. Moreover, in various forms the lens may be used in the anterior chamber, the posterior chamber sulcus and the posterior chamber bag.

Figure 4A:
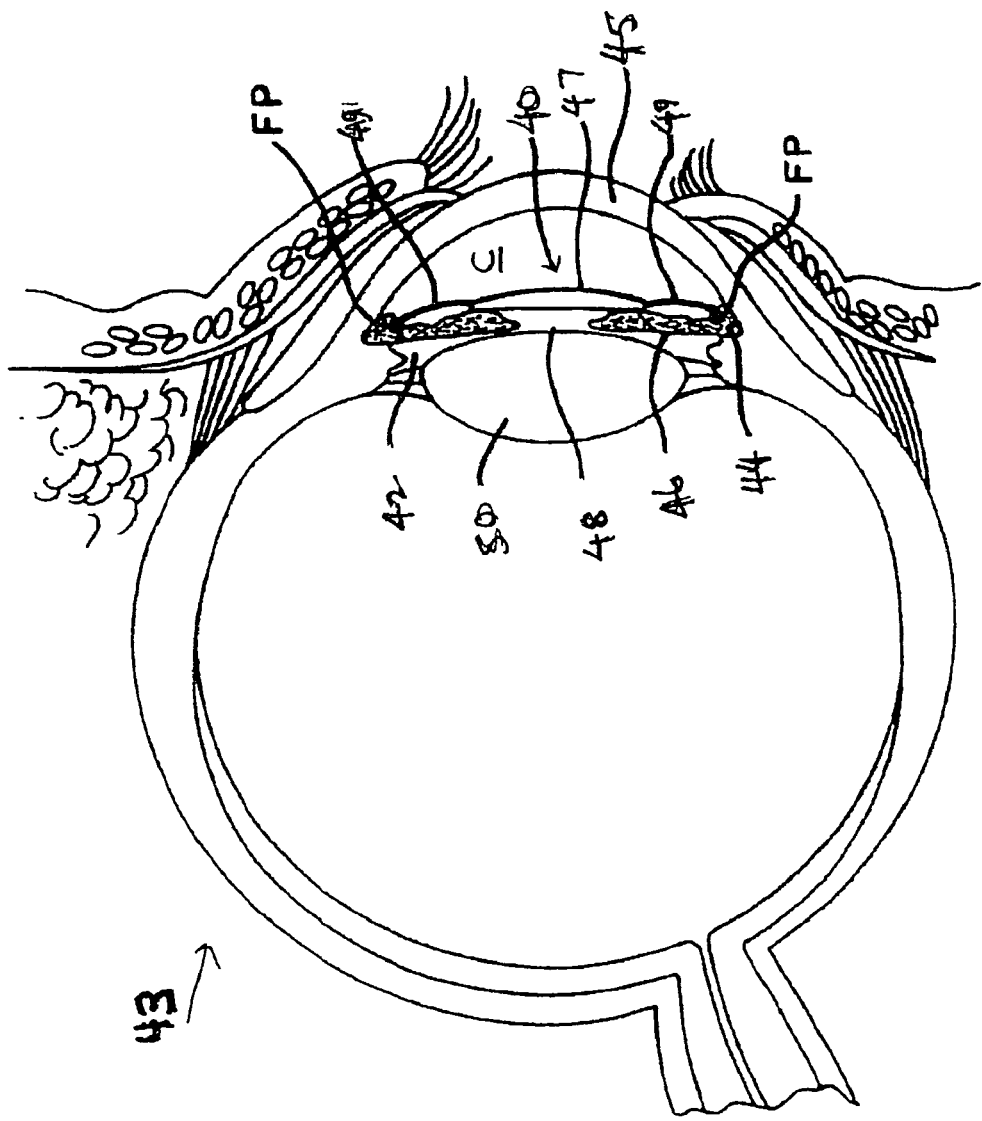
FIG. 4A shows a cross-sectional view of an eye with an phakic intraocular lens assembly of an embodiment of the present invention.

In FIG. 4A, a phakic intraocular lens assembly 40 of the invention implanted is shown, in the anterior chamber of the eye 43 and fixated in the angle 44. Alternatively, the phakic IOL of the invention may be implanted in the posterior chamber of the eye and fixated in the angle. Lens assembly 40 is positioned in anterior chamber C, between cornea 45 and iris 46. An optic 47 of assembly 40 is positioned over pupil 48.

Flexible haptics 49 extend from optic 47, with footplates FP (distal from optic 47), extending into angle 44. With the configuration, movement of natural crystalline lens 50 is unobstructed in the posterior chamber 42. The relatively low vault height of lens assembly 40 insures that it does not contact cornea 44.

Figure 4B:
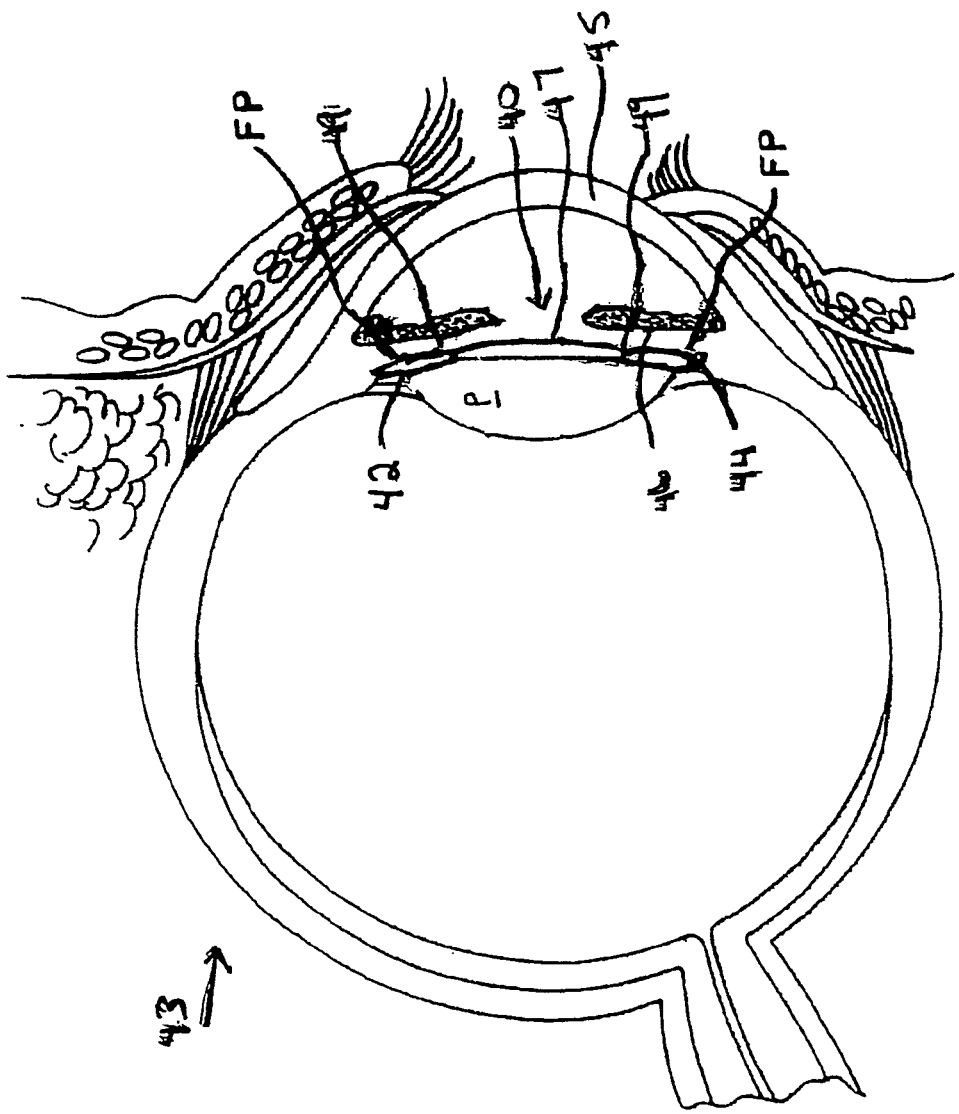
FIG. 4B shows a cross-sectional view of an eye with an aphakic intraocular lens assembly of an embodiment of the present invention.

In FIG. 4B, an aphakic intraocular lens assembly 40 of the invention is shown, implanted in the capsular bag of the eye 43. Alternatively, the aphakic IOL of the invention may be implanted in the sulcus of the eye. Lens assembly 40 is positioned in capsular bag P, behind the iris 46 and cornea 45. An optic 47 of assembly 40 has flexible haptics 49, along with footplates FP (distal from optic 47), extending into angle 44. The relatively low vault height of lens assembly 40 insures that it does not contact cornea 44.

As mentioned above, the intraocular lens assembly of the invention can be usefully implanted into the eye as either a refractive phakic intraocular lens assembly or an aphakic intraocular lens assembly. Phakic intraocular lens implantation is becoming more popular because of their good refractive and visual results and because they are relatively easy to implant in most cases (Zaldivar & Rocha, 36 Int. Ophthalmol. Clin. 107-111 (1996); Neuhann et al., 14 J. Refract. Surg. 272-279 (1998); Rosen & Gore, 24 J. Cataract Refract. Surg. 596-606 (1998); Sanders et al., 24 J. Cataract Refract. Surg. 607-611 (1998). The implantation can be performed by an ordinarily skilled ophthalmologist. Little surgical injury occurs to the ocular tissues during such implantation. When the surgical quality is not compromised, the results are highly predictable, immediate, and lasting.

Phakic lens assembly implantation using the intraocular lens assembly of the invention has advantages over other forms of surgical vision enhancement. Unlike laser surgery, the implants are removable. The natural crystalline lens remains, and the patient doesn't lose the ability to accommodate. Refractive surgery by phakic intraocular lenses among patients with hyperopia is not yet as popular as patients with myopia, but primarily because such surgery has not been available for as long (Fechner et al., 24(1) J. Cataract Refract. Surg. 48-56 (1998)).

For a phakic lens assembly implantation, the intraocular lens assembly of the invention is preferably located in the anterior chamber of the eye. Following the appropriate implantation, the intraocular lens of the assembly invention can be either an angle-supported phakic intraocular lens located in front of the iris or a sulcus-supported phakic intraocular lens located behind the iris. The haptic lens features of the intraocular lens assembly of the invention fixate the distal haptic portions of the lens, thus preventing dislocation and slipping or shifting of the intraocular lens from its proper position.

The implantation assembly of the intraocular lens assembly of the invention can generally be performed as provided by (Singh, emedicine Ophthalmology (2000) http://www.e-medicine.com/cgi-bin/foxweb.exe/showsection@d:/em/ga?book=oph&topicid=662):

First, the administration of local antibiotic drops is begun. A useful antibiotic is Tobramycin 0.3%, 1 drop, 6 times a day. Then, the pupil of the eye is contracted with 1% pilocarpine drops, administered for example at 15-minute intervals, starting 45 minutes before surgery. Drops (such as NSAID drops) are administered 2 times before surgery to minimize inflammation.

General anesthesia can be performed on the patient, but local anesthesia is preferred. For local anesthesia, 2% lidocaine with 7.5 U/ml hyaluronidase can be given 10 minutes before surgery. Orbital compression is applied to make the eye soft and to reduce orbital pressure.

For preparation of the surgical field, the periorbital skin of the patient is painted with iodine, then 5% povidine is applied. 5% povidine is also applied two-three times to the lid margin and the conjunctival fornices. Then, the eye is washed with saline.

An eye speculum is used for exposure of the surgical field. Upper and lower lid sutures, as well as superior rectus sutures can be applied in place of the speculum. (A sutureless procedure can also be used.) Adhesive plastic, applied to the surface of the eyelids, is used to pull the eyelashes.

For making small intraoperative incisions, an side port (for example, 0.6 mm) is made in the anterior chamber. This injection is started at the opposite limbus. As the aqueous fluid drains, it is replaced, for example, with a viscoelastic agent. The depth of the anterior chamber is not reduced at any time.

In one embodiment, for implantation of the intraocular lens assembly of the invention into the eye, two side ports are made to introduce the instruments that are used to fix the iris to the haptics. The width of the incision depends on the diameter of the intraocular lens assembly of the invention (being, for example, 4-5 mm). The incision may be made at the limbus or in the clear cornea. If a pocket section is made, wound closure (see, below) can be made without sutures. The intraocular lens assembly of the invention can then be introduced in the pre-crystalline space with angled-suture forceps the lens is positioned, for example, behind the iris on a horizontal axis with a cyclodialysis spatula. The intraocular lens assembly of the invention is then manipulated to center the optic on the pupil. During implantation of the phakic intraocular lens assembly of the invention into the anterior chamber, the lens is centered and fixed so that it does not slip out of position. The lens can be positioned between the cornea and the iris, but avoiding contact with either to prevent corneal damage, proliferation of corneal epithelium on the anterior surface of the lens causing opacification, or iris. If the lens is not positioned properly with respect to the pupil, too much light may be admitted to the retina, causing serious vision difficulties. The haptics generally lodge in the angle of the anterior chamber. Also, the anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The implanted lens is positioned so the flow of fluid is not blocked.

After the intraocular lens assembly of the invention is implanted, the viscoelastic material (if previously introduced into the eye chambers) is removed from the anterior and posterior chambers of the eye with an aspiration syringe (such as a 24-gauge cannula). The intraocular lens assembly of the invention is fixed to the anterior surface of the iris by the haptics of the lens. To achieve fixation, the haptic holds a fold of the iris on either side of the pupil. The anterior chamber is washed thoroughly with saline. The pupil is contracted with intraocular acetylcholine 1%, carbachol 0.01%, or pilocarpine 0.5% solution. The incision is closed by hydrating the corneal incisions. A suture rarely is needed.

In another embodiment, for implantation of the intraocular lens assembly of the invention, the main incision is made at the ventral area of the eye (at the "top" of the eye, at "12 o'clock"). The width is preferably equal to the size of the optic, which may be 4-5 mm. Side incisions are made, approximately 1 mm wide. The lens assembly of the invention is inserted then vertically. The lens assembly of the invention is rotated inside the viscoelastic-filled anterior chamber; the haptics are placed horizontally.

Fixating the lens assembly of the invention is a bimanual procedure. Lens assemblies are implanted using special tools to compress the haptics, such as forceps or cannulae, or rely on microhooks to manipulate the optic through a hole in the surface of the optic (see discussion in U.S. Pat. No. 6,142, 999). A vertically-holding lens forceps, which enters the anterior chamber through the main incision, centers the optic on the pupil and holds it steadily. A thin forceps is introduced from the side incision and grasps the iris close to the claw, passing a fold of the iris through the claw, and results in fixing one of the haptics. Both instruments are withdrawn, and the surgeon changes hands for holding each tool. The anterior chamber of the eye is again deepened with viscoelastic material, and the lens-fixation instruments are reintroduced. The second haptic-fixation maneuver is performed through the incision on the opposite side.

A peripheral iridectomy can then be performed. Then, the introduced viscoelastic material (if any) is aspirated through the three incisions. The anterior chamber is gently irrigated and inflated with air to remove all viscoelastic material.

For closure of the incision line, the apposition of the sides of the incision may be achieved by one or two superficial sutures. Alternatively, a large air bubble may be left inside the anterior chamber to effect an apposition. If the limbal incision was made without a pocket, then a closure of the incision line should be performed using sutures.

At the end of the surgery, 20 mg of gentamycin and 2 mg of dexamethasone are subconjunctivally injected. A sterile pad and a protective shield are applied.

Alternatively, the intraocular lens assembly of the invention can be located in the posterior chamber of the eye, using methods known to those of skill in the ophthalmic art (see, U.S. Pat. No. 6,110,202; Pesando et al., 15(4) J. Refract Surg. 415-23 (1999); Sanders et al., 15(3) J. Refract Surg 309-15 (1999). In posterior chamber implants, the haptics normally lodge in the ciliary sulcus.

Aphakic intraocular lens assembly implantation is also usefully provided for by the intraocular lens assembly of the invention. The lens assembly can be surgically implanted in the evacuated capsular bag of the lens of an eye (for example, through the anterior capsule opening in the bag) in a position such that the lens optic of the intraocular lens assembly is aligned with the opening defined by the anterior capsular remnant, and the outer ends of the lens distal portions are disposed within the outer perimeter of the bag. The intraocular lens assembly of the invention has a radial dimension from the outer end of each distal or extended portion to the axis of the intraocular lens assembly. Thus, with the intraocular lens assembly implanted within the capsular bag, the outer ends of the extended portions engage the inner perimetrical wall of the capsular bag with no or minimal stretching of the bag. After implantation of the intraocular lens assembly in the capsular bag, active ectodermal cells on the posterior surface of the anterior capsule rim of the bag cause fusion of the rim to the elastic posterior capsule of the bag by fibrosis about the lens extended portions. Because of the haptic design, the intraocular lens assembly of the invention can, when placed in the capsular bag of the eye, provide accommodation for the patient.

Advantageously, post-operative atropinization of the optic ciliary muscle is not required for the intraocular lens assembly of the invention (when implanted either as a refractive phakic intraocular lens or an aphakic intraocular lens) to achieve accommodation. During surgery, especially for implantation of aphakic intraocular lenses, the ciliary muscle of the eye had previously and typically been paralyzed with a ciliary muscle relaxant to place the muscle in its relaxed state. Ciliary muscle relaxants include anticholinergics such as atropine, scopolamine, homatropine, cyclopentolate and tropicarnide. Atropine is preferred. Proprietary preparations of atropine include Isopto Atropine (eye drops); Minims Atropine Sulphate (single-dose eye drops); Min-I-Jet Atropine (injection); Actonorm Powder (combined with antacids and peppermint oil); Atropine-1; Atropine-Care; Atropisol; Isopto Atropine; Ocu-tropine; Atropair; Atropine Sulfate S.O.P.; Atrosulf; 1-Tropine; Isopto Atropine; and Ocu-Tropine. Prior to this invention (i.e., while implanting intraocular lenses not having the advantages of the foldable intraocular lens assembly of the invention), the patient's eye would be atropinized following surgery, to allow for accommodation of the lens of the implanted aphakic intraocular lens assembly to the eye (see discussion, U.S. Pat. No. 6,051,024). Following surgery, the ciliary muscle relaxant (such as atropine) would be periodically introduced throughout a post-operative fibrosis and healing period (such as two to three weeks) to maintain the ciliary muscle in its relaxed state until fibrosis was complete. This drug-induced relaxation of the ciliary muscle prevented contraction of the ciliary muscle and immobilized the capsular bag. Thus, the implanted intraocular lens optic fixed during fibrosis in its distant vision position within the eye relative to the retina (accommodation). The implanted lens pressed backward against and thereby forwardly stretched the elastic posterior capsule of the capsular bag. By contrast, because of the haptic design of the intraocular lens assembly of the invention, the lens can, when placed in the capsular bag of the eye, provide accommodation for the patient without the administration of post-operative atropinc.

In another form of the present invention, there is also provided a method for implanting an intraocular lens assembly in an eye which provides accommodation. This includes the insertion of an intraocular lens (IOL) assembly into the eye, where the IOL assembly extends along an optical axis between an anterior optical surface and a posterior optical surface. The lens has a circumferential edge disposed about an optical axis at a junction of the anterior and posterior optical surfaces. The lens further includes N haptics where n is an integer greater than 1. Each haptic extends from an associated portion of the circumferential edge and along associated haptic axis. Each of the haptics is loop-like or paddle-like and extends between end portions at opposite ends thereof. The end portions are joined to the lens at the circumferential edge. Also, the haptic axis is angulated away from anterior surface by angle A with respect to a plane transverse to optical axis. In one embodiment, angle A may be in an approximate range of 4-7 degrees.

It will be apparent to those skilled in the art that other changes and modifications can be made in the above-described invention and methods for making and using the same, without departing from the scope of the invention herein, and it is intended that all matter contained in the above description shall be interpreted in an illustrative and not in a limiting sense.

What is claimed is:

1. An intraocular lens assembly, which in an at rest state prior to insertion in an eye, comprises:
   a lens extending along an optical axis between an anterior optical surface and a posterior optical surface and having a circumferential edge disposed about said optical axis at a junction of said anterior and posterior optical surfaces;

N haptics, each of said haptics extending continuously between an associated portion of said circumferential edge and a respective distal most portion of each haptic;

one footplate coupled to the distal most portion of each haptic that is configured to contact ciliary muscle of the eye or an outer perimeter of a capsular bag of the eye; and two orientation tabs extending at diametrically opposed locations from said circumferential edge, the orientation tabs arranged such that a first relative orientation of the two orientation tabs, when viewed in plan view, indicates a vaulted-forward position of the lens and a second relative orientation different from the first orientation of the two orientation tabs indicates a vaulted-reverse position of the lens;

wherein each haptic is centered about a single associated haptic axis such that each haptic is symmetric about each said single associated haptic axis, wherein N is an integer greater than 1, wherein each of said haptics has a convex, curved peripheral edge and extends between end portions at opposite ends thereof, said end portions being joined to said lens at said circumferential edge, wherein said haptics are angularly displaced with respect to said optical axis in a direction away from said anterior optical surface by an angle A in the approximate range of 4-7 degrees from a plane transverse to said optical axis.

2. An intraocular lens assembly according to claim 1, wherein each haptic forms a loop.

3. An intraocular lens assembly according to claim 1, having a first pair of haptics extending from opposite portions of said circumferential edge along an associated first pair of haptic axes, and having a second pair of haptics extending from opposite portions of said circumferential edge along an associated second pair of haptic axes, wherein said first pair of haptic axes and said optic axis are coplanar in a first haptic plane wherein said second pair of haptic axes and said optic axis are coplanar in a second haptic plane.

4. An intraocular lens assembly according to claim 3, wherein said first haptic plane is perpendicular to said second haptic plane.

5. An intraocular lens assembly according to claim 3, wherein the two orientation tabs are located between the first pair of haptic axes and the second pair of haptic axes.

6. An intraocular lens assembly according to claim 1, where each footplate is lenticular-shaped.

7. An intraocular lens assembly according to claim 1, wherein each of said haptic axes is coplanar with said optic axis in an associated haptic plane.

8. An intraocular lens assembly according to claim 1, where N is an odd number.

9. An intraocular lens assembly according to claim 8, where N=3.

10. An intraocular lens assembly according to claim 8, where N=5.

11. An intraocular lens assembly according to claim 1, where N is even.

12. An intraocular lens assembly according to claim 11, where N=2.

13. An intraocular lens assembly according to claim 11, where N=4.

14. An intraocular lens assembly according to claim 1, wherein the lens is either a monofocal or multifocal lens.

15. An intraocular lens assembly which, in an at rest state prior to insertion in an eye, comprises:

a lens extending along a single optical axis between an anterior optical surface and a posterior optical surface;

a circumferential edge disposed about said optical axis at a junction of said anterior and posterior optical surfaces;

two or more haptics, evenly distributed about the optical axis and spaced along said circumferential edge;

one footplate coupled to the distal most portion of each haptic; and two orientation tabs extending at diametrically opposed locations from said circumferential edge, the orientation tabs arranged such that a first relative orientation of the two orientation tabs, when viewed in plan view, indicates a vaulted-forward position of the lens and a second relative orientation different from the first orientation of the two orientation tabs indicates a vaulted-reverse position of the lens;

wherein each of said haptics extends outward from the circumferential edge forming a loop or paddle having a convex, curved peripheral edge, and angularly displaced with respect to said optical axis in a direction away from said anterior optical surface by an angle A from a plane transverse to said optical axis, wherein each of said haptics is centered about a single associated haptic axis such that each haptic is symmetric about each said single associated haptic axis and each of said haptics extends continuously between the circumferential edge and a respective distal most portion of each haptic, wherein the footplate coupled to the distal most portion of each haptic is configured to contact ciliary muscle of the eye or an outer perimeter of a capsular bag of the eye.

16. An intraocular lens assembly according to claim 15, having a first pair of haptics extending from opposite portions of said circumferential edge along an associated first pair of haptic axes, and having a second pair of haptics extending from opposite portions of said circumferential edge along an associated second pair of haptic axes, wherein said first pair of haptic axes and said optic axis are coplanar in a first haptic plane wherein said second pair of haptic axes and said optic axis are coplanar in a second haptic plane.

17. An intraocular lens assembly according to claim 16, wherein said first haptic plane is perpendicular to said second haptic plane.

18. An intraocular lens assembly according to claim 15, wherein each haptic forms a loop.

19. An intraocular lens assembly according to claim 15, wherein each haptic forms a paddle.

* * * * *